United States Patent [19]

Spivey et al.

[11] Patent Number: 5,710,328
[45] Date of Patent: Jan. 20, 1998

[54] PREPARATION OF α, β-UNSATURATED CARBOXYLIC ACIDS AND ANHYDRIDES

[75] Inventors: James Jerry Spivey, Cary; Makarand Ratnakav Gogate, Durham, both of N.C.; Joseph Robert Zoeller; Gerald Charles Tustin, both of Kingsport, Tenn.

[73] Assignee: Eastman Chemical Company, Kingsport, Tenn.

[21] Appl. No.: 562,860

[22] Filed: Nov. 27, 1995

[51] Int. Cl.$^6$ .................................................. C07C 51/00
[52] U.S. Cl. ..................................................... 562/599
[58] Field of Search ........................................ 562/599

[56] References Cited

U.S. PATENT DOCUMENTS

| | | | |
|---|---|---|---|
| 3,238,253 | 3/1966 | Kerr | 260/530 |
| 4,085,143 | 4/1978 | Holmes | 260/515 R |
| 4,581,471 | 4/1986 | Barlow et al. | 560/210 |

OTHER PUBLICATIONS

M. Ai, *J. Catal.*, 107, 201 (1987) Apr. 1987.
M. Ai, *J. Catal.*, 124, 293 (1990).
M. Ai, *Appl. Catal.*, 36, 221 (1988).
M. Ai, *Appl. Catal.*, 63, 29 (1990).
M. Ai, *Bull. Chem. Soc. Jap.*, 63, 1217 (1990).
M. Ai, *Bull. Chem. Soc. Jap.*, 63, 3722 (1990).
M. Ai, *Appl. Catal.*, 48, 51 (1989, primarily catalyst preparation).
E.G. Hancock, "Catalyst Types of Interest in the Oxidation of Propylene to Acrylic Acid", Propylene and Its Industrial Derivatives, Chapter 10, pp. 367–415, 1973.

*Primary Examiner*—Gary Geist
*Assistant Examiner*—Rosalynd Keys
*Attorney, Agent, or Firm*—Michael J. Blake; J. Frederick Thomsen; Harry J. Gwinnell

[57] ABSTRACT

Disclosed is a process for the preparation of α,β-unsaturated carboxylic acids and anhydrides thereof which comprises contacting formaldehyde or a source of formaldehyde with a carboxylic anhydride in the presence of a catalyst comprising mixed oxides of vanadium, phosphorus and, optionally, a third component selected from titanium, aluminum or, preferably silicon.

3 Claims, No Drawings

PREPARATION OF α, β-UNSATURATED CARBOXYLIC ACIDS AND ANHYDRIDES

This invention was made with Government Support under DOE Contract No. DE-AC22-94PC94065 awarded by the Department of Energy. The Government has certain rights in this invention.

This invention pertains to a process for the preparation of α,β-unsaturated carboxylic acids and anhydrides by the condensation of formaldehyde with aliphatic carboxylic anhydrides. More specifically, this invention pertains to the synthesis of α,β-unsaturated carboxylic acids and anhydrides by the condensation of formaldehyde with aliphatic carboxylic anhydrides in the presence of a catalyst comprising oxides of vanadium and phosphorus, preferably supported on oxides, including mixed oxides, of silicon, titanium, and/or aluminum.

α,β-Unsaturated acids, particularly acrylic and methacrylic acid, and their ester derivatives are among the most useful organic compounds in the chemical industry wherein their polymerization products find a myriad of applications including plastic sheeting for signs, coatings (including latex paints), adhesives, fibers, and synthetic resins. Given their utility, it would be useful to find alternative processes for the generation of these materials. This is particularly true for the generation of methacrylic acid and its derivatives since the process presently used for the generation of methacrylic acid produces copious quantities of waste and, therefore, represents a challenge to the environment.

The prior art contains numerous references to the condensation of formaldehyde with carboxylic acids and alkyl carboxylate esters according to the equation:

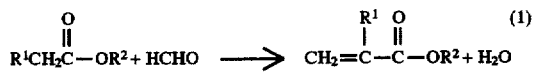

wherein $R^1$ and $R^2$ independently are selected from hydrogen and alkyl. The condensation of carboxylic acids or esters over unsupported catalysts consisting of mixed oxides of V and P is described by M. Ai, *J. Catal.*, 107, 201 (1987); M. Ai, *J. Catal.*, 124, 293 (1990); M. Ai, *Appl. Catal.*, 36, 221 (1988); M. Ai, Shokubai, 29, 522 (1987); and M. So, JP 01068336 A2. The condensation of carboxylic acids or esters over catalysts consisting of mixed oxides of V and P on oxides of silicon is described by M. Ai, *Appl. Catal.*, 63, 29 (1990); M. Ai, *Bull. Chem. Soc. Jap.*, 63, 1217 (1990); and M. Ai, *Bull. Chem. Soc. Jap.*, 63, 3722 (1990). The same condensation in the presence of catalysts consisting of mixed oxides of V and P on oxides of titanium is disclosed by M. Ai, *Studies in Surface Sci. and Catal.*, 72, 101 (1992); M. Ai, *Appl. Catal.*, 54, 29 (1989); M. Ai, *Proc. - Int. Congr. Catal.*, 9th (1988) Vol. 4, 1562; M. Ai, *Appl. Catal.*, 48, 51 (1989, primarily catalyst preparation); M. Ai, *J. Catal.*, 113, 562 (1988, primarily catalyst preparation); M. Ai, Shokubai, 30, 420 (1988); M. So, JP 01068334; and M. So, JP 01068337.

There are certain disadvantages inherent in the use of a carboxylic acid or ester in the condensation reaction depicted in Equation (1). For example, the condensation of formaldehyde with a carboxylic acid or ester produces an equivalent of water. It is probable that the water produced will inhibit further reaction of additional carboxylic acid and formaldehyde and, in the case of ester feedstocks, also will cause hydrolysis of the ester. Furthermore, water is likely to complicate downstream processing since provisions need to be made for its removal.

The synthesis of α,β-unsaturated carboxylic acids and anhydrides thereof by the condensation of formaldehyde with aliphatic carboxylic anhydrides according to Equation (2) is described by Holmes, U.S. Pat. No. 4,085,143:

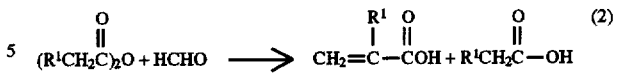

The coproduced aliphatic carboxylic acid can be used to regenerate the corresponding carboxylic acid anhydride by any of several known processes. See, for example, the processes disclosed by Cook, "Acetic Anhydride", Chap. 9 in V. H. Agreda and J. R. Zoeller, eds. *Acetic Acid and Its Derivatives*, Marcel Dekker, Inc., New York, N.Y. (USA) (1993), p. 145, and, for the generation of propionic anhydride from propionic acid, ethylene, and carbon monoxide, see U.S. Pat. Nos. 2,658,075, 2,497,304, 3,989,751, 2,593,440, 4,335,058 and 4,483,803. Unfortunately, as noted by Holmes (U.S. Pat. No. 4,085,143) and exploited by Toland and Lapporte U.S. Pat. Nos. 3,927,078 and 3,812,176, the interaction of anhydrides with aliphatic aldehydes, including formaldehyde, generally leads not to condensation, but to the formation of 1,1-dicarboxylates, at least in the condensed phase according to Equation (3):

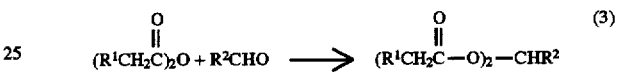

As a consequence, the condensation of aldehydes and anhydrides has seen limited application outside of the well documented condensation with aromatic aldehydes which do not form the diesters readily. (The condensation of anhydrides with aromatic aldehydes is known as the Perkin reaction.) Despite the potential advantages offered by the synthesis of α,β-unsaturated carboxylic acids and anhydrides thereof by the condensation of formaldehyde with aliphatic carboxylic anhydrides, prior art descriptions of such condensations have been limited to U.S. Pat. No. 4,085,143 and S. Oda, T. Nakano, R. Han, JP 06048977 A2.

We have now discovered that mixed oxides of vanadium and phosphorus, preferably in the presence of, or supported upon, an additional oxide, such as titania, silica, alumina, or their mixed oxides, are effective catalysts for the condensation of formaldehyde and carboxylic acid anhydrides to generate α,β-unsaturated carboxylic acids and their anhydrides. The present invention therefore provides a process for the preparation of α,β-unsaturated carboxylic acids and anhydrides thereof which comprises reacting or contacting formaldehyde or a source of formaldehyde with a carboxylic anhydride in the presence of a catalyst comprising mixed oxides of vanadium and phosphorus. The catalysts utilized in the present invention preferably comprise mixed oxides of vanadium and phosphorus in admixture with or supported on another oxide selected from oxides of titanium, silicon, aluminum and mixed oxides of 2 or more thereof. The reaction or condensation involved in our novel process is depicted by Equation (2):

The vanadium:phosphorus atomic ratio of the mixed oxide catalysts utilized in the present invention may be in the range of about 1:0.1 to 1:50, preferably 1:1 to 1:10. When using the preferred catalysts which contain at least one additional oxide, e.g., titania, silica and/or alumina, in admixture with or as a support material for the mixed vanadium-phosphorus oxides, the atomic ratio of V to Ti, Si and/or Al may be in the range of about 1:1 to 1:100 but preferably is in the range of about 1:5 to 1:25. A preferred catalyst comprises a mixture of oxides of vanadium, silicon and phosphorus, particularly catalysts consisting essentially of materials having the formula (excluding oxygen):

in which the ratio of x:w:y is in the range of about 1:8–12:2–4. The catalysts employed in the process of the present invention may be prepared by known methods such as the procedures published in the references cited above.

The carboxylic anhydride reactants which may be used in the present invention have the general formula:

wherein $R^1$ is hydrogen, alkyl of up to about 20 carbon atoms, alkenyl of up to about 20 carbon atoms, or aryl including alkyl substituted aryl of 6 to 10 carbon atoms, e.g., phenyl, tolyl, xylyl, naphthyl, etc. The anhydride reactants of particular interest are the anhydrides of acetic and propionic acid.

The formaldehyde reactant may be provided in a variety of forms, although solutions which are reactive with the anhydride, such as the commonly available aqueous and methanolic solutions, obviously are deleterious. Therefore, the formaldehyde reactant preferably is provided as gaseous formaldehyde, trioxane, or paraformaldehyde. Although the formaldehyde may be added in excess, it is operationally preferable to add the carboxylic acid anhydride in excess of the formaldehyde. The mole ratio of carboxylic acid anhydride to formaldehyde (or formaldehyde equivalent) can range from about 1:1 to 50:1 with the preferred range being about 2:1 to 15:1.

Although it is possible to operate the process in the liquid phase, for example by utilizing superatmospheric pressures, we prefer to carry out the process in the vapor phase wherein the reactants are vaporized prior to contact with the catalyst. The vapor can be added with or without a non-reactive (inert) diluent gas such as nitrogen, methane, helium, argon, etc. However, the use of such a nonreactive diluent gas does not provide any advantage to the operation of the process. The gaseous flow rates used in the practice of the process may be varied widely and are a matter of empirical optimization for each catalyst and anhydride combination. The gas flow rate typically will be in the range of about 10 to 10,000 liters per kilogram catalyst per hour with a range of about 100 to 1000 L/kg catalyst-hour being preferred.

The process may be operated over a wide range of temperatures and pressures. However, since operation preferably is in the vapor phase, the pressure and temperature chosen should be sufficient to operate above the dew point which is a function of the carboxylic anhydride chosen, the pressure, the temperature, and, if a nonreactive, diluent or carrier gas is used, the concentration of the carboxylic anhydride in the carrier gas. This mode of operation still permits a wide range of conditions but, in general, will require a temperature of about 100° to 650° C., the preferred range being about 200° to 350° C. Reaction pressure may be in the range of about 0.1 to 50 bars absolute with a range of about 0.5 to 5 bars absolute being preferred. The process normally is operated under substantially anhydrous conditions, meaning that no extraneous water is added during the operation of the process. Water, of course, is coproduced in the condensation and the feed materials may contain minor amounts, e.g., up to 500 ppm, water as impurity.

Like most heterogeneous catalysts, the vanadium-phosphorus-based catalysts utilized in the present invention are prone to deactivation. The activity of these catalysts may be readily restored by oxidation with oxygen-containing gas, preferably air, at elevated temperatures. For example, reactivation may be carried out at temperatures in the range of 150° to 500° C., preferably at 250° to 350° C.

The process of the present invention and the preparation of catalyst used therein are further illustrated by the following examples.

CATALYST PREPARATION

CATALYST EXAMPLE 1

To 480 mL of colloidal silica consisting of 30 weight percent silica in water (DuPont Ludox® SM-30) was added (i) a solution of 23.4 g $NH_4VO_3$ in 100 mL of hot water containing 20 mL of lactic acid and (ii) a solution of 64.4 g of 85% $H_3PO_4$ in 100 mL hot water. The mixture was stirred at 50° C. to evaporate water and the cake obtained was dried in an oven in which the temperature was increased from 50° C. to 200° C. at the rate of 1° C. per minute. The resulting solid was crushed and a portion having a 8–20 mesh particle size (2.8–0.2 mm) was calcined in air first at 350° C. for 6 hours and then at 450° C. for 6 hours. The catalyst obtained (Catalyst I) consisted of vanadium, silicon and phosphorus in a V:Si:P atomic ratio of 1:12:2.8.

The general procedure described in Catalyst Example 1 was used to prepare additional catalyst consisting of vanadium, silicon and phosphorus in a V:Si:P atomic ratio of 1:10:2.8 (Catalyst II); 1:2.8:2.8 (Catalyst III); 1:3.57:1 (Catalyst IV); and 1:10:10 (Catalyst V).

CATALYST EXAMPLE 2

To 500 mL of chilled water was added dropwise 20 mL of $TiCl_4$ and the resulting solution was diluted with 2 L water and dilute aqueous ammonia to form a precipitate of titanium hydroxide (final pH 8.5). The precipitate was washed with water 5 times by decantation and then filtered to yield a paste-like, hydroxide gel. To about 200 mL water containing 50 mL lactic acid was added 9.7 g of $NH_4VO_3$ and the mixture was warmed slowly to yield a clear blue solution. The titanium hydroxide gel was mixed with 57 g of 85% $H_3PO_4$ to produce a sticky white syrup which then was combined with the clear blue solution. The mixture was stirred at 50° C. to evaporate water and the light blue cake obtained was dried in an oven in which the temperature was increased from 50° C. to 200° C. at the rate of 1° C. per minute. The resulting solid was calcined at 300° C. for 6 hours in a stream of air, then ground, classified, and a portion having a 8–20 mesh particle size (2.8 to 0.2 mm) was calcined again in air at 450° C. for 6 hours. The catalyst obtained (Catalyst VI) consisted of vanadium, titanium and phosphorus in a V:Ti:P atomic ratio of 1:2:6.

INVENTION EXAMPLES

The examples described below were carried out in a microreactor consisting of (1) a 40.6 cm (16 inch) section of 316 stainless steel tubing having an inside diameter of 1.25 cm (0.5 inch) which functioned as a preheater and (2) a 35.6 cm (14 inch) section of 316 stainless steel tubing having an inside diameter of 1.25 cm (0.5 inch) which served as the reactor. The preheater was filled with quartz beads and the catalyst was placed in the reactor. The space remaining in the reactor was filled with quartz beads and the beads and catalyst were held in place by the insertion of quartz wool in the reactor tube. The preheater and reactor tube were aligned horizontally, connected by short, well-insulated, stainless steel tubing, and each section placed in a separate electric furnace. A thermocouple was positioned in the catalyst bed. To the inlet of the preheater was connected a nitrogen feed line and a liquid feed line. The exit port of the reactor was connected to a condenser and liquid samples were collected after condensation. The gas outlet of the reactor system was connected to an outlet and an on-line gas chromatograph.

The microreactor was operated by heating the preheater to 300° C. and introducing a continuous nitrogen purge of 220 millimoles per hour (mmol/hour) through the system with the pressure maintained at about 3 bars absolute. Using the thermocouple in the reactor section as a thermostat, the reactor tube then was heated to and maintained at 300° C. throughout the reaction.

A solution of 2.25 g (0.025 mol) of 1,3,5-trioxane (formaldehyde trimer) in 20 g (0.15 mol) of propionic anhydride (propionic anhydride:formaldehyde molar ratio of 2:1) was introduced to the preheater at a rate of about 6 g per hour (40 mmol/hour propionic anhydride, 20 mmol/hour formaldehyde) via the liquid feed line. This combination results in a nominal gas feed rate of 290 L/Kg catalyst-hour.

The 300° C. preheater temperature is sufficient to both vaporize the propionic anhydride and convert the trioxane to gaseous monomeric formaldehyde. The vaporized components are swept to, and through, the reactor tube by the nitrogen purge. After passage through the reactor tube the liquid components are condensed, weighed, and analyzed by GC for diethyl ketone, propionic acid, propionic anhydride, methacrylic acid, and methacrylic anhydride. (The last component is generally minor.) The gaseous effluent is analyzed periodically for CO and $CO_2$.

EXAMPLE 1-4

Four experiments, each of a duration of 2.58 hours, were carried out using the above-described procedure and varying amounts of Catalyst II which resulted in varying gas feed rates. Table I shows the amounts (g) of Catalyst II used, the gas feed rate (Feed Rate, L/kg catalyst/hour) and rate of formation of methacrylic acid (Production Rate, moles methacrylic acid produced per kg catalyst per hour).

TABLE I

| Example | Catalyst | Feed Rate | Production Rate |
|---|---|---|---|
| 1 | 16.5 | 290 | 1.25 |
| 2 | 15 | 320 | 0.66 |
| 3 | 10 | 480 | 0.89 |
| 4 | 5 | 900 | 1.23 |

EXAMPLES 5-8

Four additional experiments, each of a duration of 2.58 hours, were carried out using the above-described procedure and 15 g of each of Catalyst I, III, IV or V to determine the effect of varying the atomic ratios of vanadium, silicon and phosphorus. The feed rate in each of the experiments of Examples 5-8 (as well as Example 2 above) was 320 L/kg-catalyst per hour. The results obtained are shown in Table II wherein Catalyst refers to the particular catalyst (specified in Catalyst Example 1) used in each experiment and Production Rate has the meaning given above.

TABLE II

| Example | Catalyst | Production Rate |
|---|---|---|
| 5 | I | 0.62 |
| 2 | II | 0.66 |
| 6 | III | 0.45 |
| 7 | IV | 0.46 |
| 8 | V | 0.11 |

COMPARATIVE EXAMPLES C-1–C-3

In Comparative Example C-1, Examples 3 was repeated except that the propionic anhydride used in the feed mixture was replaced with propionic acid (5.33 g per hour, 72 mmol per hour). In Comparative Examples C-2 and C-3, Examples 2 and 4 were repeated except that the propionic anhydride used in the feed mixture was replaced with methyl propionate (5.37 g per hour, 61 mmol per hour). The results obtained are shown in Table III wherein the values given under Catalyst refer to the amount (g) of Catalyst II used in each of Comparative Examples C-1–C-3 and Feed rate and Production Rate have the meanings given above except that the values given for Production Rate in Examples C-2 and C-3 are for the total moles of methacrylic acid and methyl methacrylate produced per kg catalyst per hour. The values obtained in Examples 2–4 are provided in Table III for comparison.

TABLE III

| Example | Catalyst | Feed Rate | Production Rate |
|---|---|---|---|
| 2 | 15 | 320 | 0.66 |
| C-2 | 15 | 320 | 0.20 |
| 3 | 10 | 480 | 0.89 |
| C-1 | 10 | 480 | 0.57 |
| 4 | 5 | 900 | 1.23 |
| C-3 | 5 | 900 | 0.23 |

EXAMPLE 9

Example 1 was repeated using 1 g of Catalyst VI described in Catalyst Example 2 and a reactor temperature of 400° C. The amount of methacrylic acid produced corresponded to approximately only 30% of the amount obtained using the catalysts consisting of vanadium, silicon and phosphorus. Therefore, the catalysts consisting of vanadium, titanium and phosphorus, while useful to produce methacrylic acid, are inferior to catalysts consisting of vanadium, silicon and phosphorus, although optimization of the V:Ti:P atomic ratio of the former may improve their usefulness.

The invention has been described in detail with particular reference to preferred embodiments thereof, but it will be understood that variations and modifications can be effected within the spirit and scope of the invention.

We claim:

1. Process for the preparation of $\alpha,\beta$-unsaturated carboxylic acids and anhydrides thereof which comprises contacting formaldehyde or a source of formaldehyde with a carboxylic anhydride in the presence of a catalyst comprising mixed oxides of vanadium and phosphorus.

2. Process according to claim 1 for the preparation of an $\alpha,\beta$-unsaturated carboxylic acid having the formula

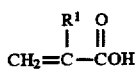

which comprises contacting formaldehyde or a source of formaldehyde with a carboxylic anhydride having the formula

at a temperature of 150° to 500° C. in the presence of a vanadium-phosphorus mixed oxide catalyst wherein the vanadium:phosphorus atomic ratio is in the range of about 1:0.1 to 1:50 and wherein $R^1$ is hydrogen, alkyl of up to about 20 carbon atoms, alkenyl of up to about 20 carbon atoms, or aryl of 6 to 10 carbon atoms.

3. Process for the preparation of an α,β-unsaturated carboxylic acid having the formula

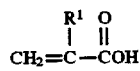

which comprises contacting in the gas phase formaldehyde or a source of formaldehyde with a carboxylic anhydride having the formula

at a temperature of 250° to 350° C. in the presence of a catalyst comprising the oxides of vanadium, silicon and phosphorus having the formula (excluding oxygen):

in which the ratio of x:w:y is in the range of about 1:8–12:2–4; and wherein $R^1$ is hydrogen or methyl.

* * * * *